[(12) United States Patent]{} Gulevich et al.

(10) Patent No.: US 7,771,976 B2
(45) Date of Patent: Aug. 10, 2010

(54) **METHOD FOR PRODUCING A NON-AROMATIC L-AMINO ACID USING A BACTERIUM OF THE *ENTEROBACTERIACEAE* FAMILY HAVING EXPRESSION OF THE CSRA GENE ATTENUATED**

(75) Inventors: Andrey Yurievich Gulevich, Moscow (RU); Danila Vadimovich Zimenkov, Moscow (RU); Elena Vitalievna Klyachko, Moscow (RU); Tatyana Viktorovna Leonova, Moscow (RU); Yury Ivanovich Koslov, Moscow (RU); Vitaly Grigorievich Paraskevov, legal representative, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 300 days.

(21) Appl. No.: 11/830,969

(22) Filed: Jul. 31, 2007

(65) Prior Publication Data

US 2009/0239266 A1    Sep. 24, 2009

Related U.S. Application Data

(63) Continuation of application No. PCT/JP2006/303211, filed on Feb. 16, 2006.

(60) Provisional application No. 60/714,850, filed on Sep. 8, 2005.

(30) Foreign Application Priority Data

Feb. 18, 2005    (RU) .............................. 2005104459

(51) Int. Cl.
*C12P 13/08* (2006.01)
*C12P 13/04* (2006.01)
*C12P 13/24* (2006.01)
*C12P 13/20* (2006.01)
*C12P 13/14* (2006.01)
*C12P 13/12* (2006.01)
*C12P 13/06* (2006.01)
*C12N 1/20* (2006.01)
*C07K 14/00* (2006.01)
*C07H 21/02* (2006.01)

(52) U.S. Cl. ....................... 435/115; 435/106; 435/107; 435/109; 435/110; 435/113; 435/116; 435/252.3; 530/350; 536/23.1

(58) Field of Classification Search ........................ None
See application file for complete search history.

(56) References Cited

U.S. PATENT DOCUMENTS

| | | | |
|---|---|---|---|
| 5,684,144 A | 11/1997 | Romeo | |
| 6,960,455 B2 | 11/2005 | Livshits et al. | |
| 7,138,266 B2 | 11/2006 | Debabov et al. | |
| 7,179,623 B2 | 2/2007 | Livshits et al. | |
| 7,186,531 B2 | 3/2007 | Akhverdian et al. | |
| 2004/0132165 A1 | 7/2004 | Akhverdian et al. | |
| 2005/0048631 A1 | 3/2005 | Klyachko et al. | |
| 2005/0054061 A1 | 3/2005 | Klyachko et al. | |
| 2005/0176033 A1 | 8/2005 | Klyachko et al. | |
| 2005/0191684 A1 | 9/2005 | Zimenkov et al. | |
| 2005/0214911 A1 | 9/2005 | Marchenko et al. | |
| 2006/0014257 A1 | 1/2006 | Katashkina et al. | |
| 2006/0035346 A1 | 2/2006 | Savrasova et al. | |
| 2006/0035348 A1 | 2/2006 | Gulevich et al. | |
| 2006/0040365 A1 | 2/2006 | Kozlov et al. | |
| 2006/0088919 A1 | 4/2006 | Rybak et al. | |
| 2006/0141586 A1 | 6/2006 | Rybak et al. | |
| 2006/0160192 A1 | 7/2006 | Rybak et al. | |
| 2006/0286643 A1 | 12/2006 | Sheremet'eva et al. | |
| 2007/0184532 A1 | 8/2007 | Klyachko et al. | |

FOREIGN PATENT DOCUMENTS

| | | |
|---|---|---|
| WO | WO99/02721 | 1/1999 |
| WO | WO00/73484 | 12/2000 |
| WO | WO03/046184 | 6/2003 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
U.S. Appl. No. 60/586,222, filed Jul. 9, 2004, Akhverdian et al.
U.S. Appl. No. 60/587,492, filed Jul. 14, 2004, Klyachko et al.
U.S. Appl. No. 60/604,698, filed Aug. 27, 2004, Zimenkov et al.
U.S. Appl. No. 60/610,545, filed Sep. 17, 2004, Marchenko et al.
U.S. Appl. No. 60/644,562, filed Jan. 19, 2005, Rybak et al.
U.S. Appl. No. 60/673,807, filed Apr. 22, 2005, Rybak et al.
U.S. Appl. No. 60/693,507, filed Jun. 24, 2005, Rybak et al.
U.S. Appl. No. 60/693,509, filed Jun. 24, 2005, Sheremet'eva et al.
U.S. Appl. No. 60/703,414, filed Jul. 29, 2005, Ptitsyn et al.
U.S. Appl. No. 60/703,426, filed Jul. 29, 2005, Rybak et al.
U.S. Appl. No. 60/714,843, filed Sep. 8, 2005, Filippov et al.
U.S. Appl. No. 60/714,850, filed Sep. 8, 2005, Gulevich et al.
U.S. Appl. No. 60/723,566, filed Oct. 5, 2005, Rybak et al.
U.S. Appl. No. 60/723,924, filed Oct. 6, 2005, Rybak et al.
U.S. Appl. No. 60/723,925, filed Oct. 6, 2005, Rybak et al.
U.S. Appl. No. 11/275,507, filed Jan. 11, 2006, Ptitsyn et al.
U.S. Appl. No. 60/743,222, filed Feb. 3, 2006, Rybak et al.
U.S. Appl. No. 60/743,223, filed Feb. 3, 2006, Rybak et al.
U.S. Appl. No. 60/743,257, filed Feb. 9, 2006, Rybak et al.
U.S. Appl. No. 60/743,258, filed Feb. 9, 2006, Rybak et al.
U.S. Appl. No. 60/806,819, filed Jul. 10, 2006, Rybak et al.
U.S. Appl. No. 60/807,845, filed Jul. 20, 2006, Filippov et al.
U.S. Appl. No. 60/826,820, filed Sep. 25, 2006, Kotliarova et al.
U.S. Appl. No. 11/536,863, filed Sep. 29, 2006, Zakataeva et al.
U.S. Appl. No. 60/829,706, filed Oct. 17, 2006, Filippov et al.

(Continued)

*Primary Examiner*—Christian L Fronda
(74) *Attorney, Agent, or Firm*—Shelly Guest Cermak; Cermak Nakajima LLP (57) ABSTRACT

The present invention provides a method for producing a non-aromatic L-amino acid using a bacterium of the Enterobacteriaceae family, particularly a bacterium belonging to the genus *Escherichia* or *Pantoea*, which has been modified to attenuate expression of the csrA gene.

5 Claims, 2 Drawing Sheets

OTHER PUBLICATIONS

U.S. Appl. No. 60/867,151, filed Nov. 24, 2006, Kotliarova et al.
U.S. Appl. No. 60/885,671, filed Jan. 19, 2007, Ptitsyn et al.
U.S. Appl. No. 60/894,996, filed Mar. 15, 2007, Rybak et al.
U.S. Appl. No. 11/830,961, filed Jul. 31, 2007, Filippov et al.
International Search Report for PCT Patent App. No. PCT/JP2006/303211 (May 30, 2006).
International Preliminary Report on Patentability for PCT Patent App. No. PCT/JP2006/303211 (Aug. 30, 2007).
Jackson, D. W., et al., "Biofilm Formation and Dispersal under the Influence of the Global Regulator CsrA of *Escherichia coli*," J. Bacteriol. 2002;184(1):290-301.

Romeo, T., et al., "Identification and Molecular Characterization of *csrA*, a Pleiotropic Gene from *Escherichia coli* That Affects Glycogen Biosynthesis, Gluconeogenesis, Cell Size, and Surface Properties," J. Bacteriol. 1993;175(15):4744-4755.

Sabnis, N. A., et al., "Pleiotropic Regulation of Central Carbohydrate Metabolism in *Escherichia coli* via the Gene *csrA*," J. Biol. Chem. 1995;270(49):29096-29104.

Yang, H., et al., "Coordinate Genetic Regulation of Glycogen Catabolism and Biosynthesis in *Escherichia coli* via the CsrA Gene Product," J. Bacteriol. 1996;178(4):1012-1017.

* cited by examiner

METHOD FOR PRODUCING A NON-AROMATIC L-AMINO ACID USING A BACTERIUM OF THE *ENTEROBACTERIACEAE* FAMILY HAVING EXPRESSION OF THE CSRA GENE ATTENUATED

This application claims priority under 35 U.S.C. § 119 to Russian Patent Application No. 2005104459, filed on Feb. 18, 2005, and U.S. Provisional Patent Application No. 60/714,850, filed on Sep. 8, 2005, and under 35 U.S.C. §120 as a continuation to PCT/JP2006/303211, filed Feb. 16, 2006, the contents of all of which are incorporated by reference in their entireties. The Sequence Listing filed electronically herewith is also hereby incorporated by reference in its entirety (File Name: US-204_Seq_List_Copy_1; File Size: 3 KB; Date Created: Jul. 31, 2007).

BACKGROUND OF THE INVENTION

1. Field of the Invention

The present invention relates to the microbiological industry, and specifically to a method for producing a non-aromatic L-amino acid using a bacterium of the Enterobacteriaceae family which has been modified to attenuate expression of the csrA gene.

2. Brief Description of the Related Art

The CsrA protein encoded by a pleiotropic gene csrA from *Escherichia coli* is a regulator of carbohydrate metabolism which affects glycogen biosynthesis, gluconeogenesis, cell size and surface properties (Romeo, T et al, J. Bacteriol., 175(15): 4744-4755 (1993)), glycogen degradation (Yang, H. et al, J. Bacteriol., 178(4):1012-7 (1996)), gluconeogenesis and glycolysis (Sabnis, N. A. et al, J. Biol. Chem., 270, 49, 29096-29104 (1995)). The CsrA protein also plays a regulatory role in biofilm dynamics (Jackson, D. W., J. Bacteriol., 184(1): 290-301 (2002)).

A microorganism having increased synthesis of aromatic compounds, useful particularly for producing phenylalanine, having decreased carbon storage regulator (CsrA) protein activity, and having increased content of erythrose-4-phosphate has been disclosed (WO0073484A1).

A process for the preparation of non-aromatic L-amino acids, in particular L-threonine, by fermentation of microorganisms of the Enterobacteriaceae family in which the csrA gene or nucleotide sequences which code for it are enhanced, in particular over-expressed, has also been disclosed (WO03046184A1).

But currently, there have been no reports of inactivating the csrA gene for the purpose of producing non-aromatic L-amino acids.

SUMMARY OF THE INVENTION

Objects of the present invention include enhancing the productivity of non-aromatic L-amino acid producing strains and providing a method for producing an non-aromatic L-amino acid using these strains.

The above objects were achieved by finding that attenuating expression of the csrA gene can enhance production of non-aromatic L-amino acids, such as L-threonine, L-lysine, L-cysteine, L-leucine, L-histidine, L-glutamic acid, L-proline, and L-arginine.

The present invention provides a bacterium of the Enterobacteriaceae family having an increased ability to produce non-aromatic L-amino acids, such as L-threonine, L-lysine, L-cysteine, L-leucine, L-histidine, L-glutamic acid, L-proline, and L-arginine.

It is an object of the present invention to provide a non-aromatic L-amino acid producing bacterium of the Enterobacteriaceae family, wherein the bacterium has been modified to attenuate expression of the csrA gene.

It is a further object of the present invention to provide the bacterium as described above, wherein the expression of the csrA gene is attenuated by inactivation of the csrA gene.

It is a further object of the present invention to provide the bacterium as described above, wherein the bacterium belongs to the genus *Escherichia*.

It is a further object of the present invention to provide the bacterium as described above, wherein the bacterium belongs to the genus *Pantoea*.

It is a further object of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine.

It is a further object of the present invention to provide a method for producing a non-aromatic L-amino acid comprising:

cultivating the bacterium as described above in a medium to produce and excrete said non-aromatic L-amino acid into the medium, and collecting said non-aromatic L-amino acid from the medium.

It is a further object of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine.

The present invention is described in detail below.

DESCRIPTION OF THE PREFERRED EMBODIMENTS

1 Bacterium of the Present Invention

The bacterium of the present invention is a non-aromatic L-amino acid producing bacterium of the Enterobacteriaceae family, wherein the bacterium has been modified to attenuate expression of the csrA gene.

In the present invention, "non-aromatic L-amino acid producing bacterium" means a bacterium which has an ability to produce and excrete a non-aromatic L-amino acid into a medium, when the bacterium is cultured in the medium.

The phrase "non-aromatic L-amino acid-producing bacterium" as used herein also means a bacterium which is able to produce and cause accumulation of an non-aromatic L-amino acid in a culture medium in an amount larger than a wild-type or parental strain of *E. coli*, such as *E. coli* K-12, and preferably means that the microorganism is able to cause accumulation in a medium of an amount not less than 0.5 g/L, more preferably not less than 1.0 g/L of the target L-amino acid. The term "non-aromatic L-amino acid" comprises L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-proline and L-arginine are particularly preferred.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella Yersinia*, etc. Specifically, those classified into the Enterobacteriaceae according to the taxonomy used in the NCBI (National Center for Biotechnology Information) database (http://www.ncbi.nlm.nih.gov/ht-binpost/Taxonomy/wgetorg?mode=Tree&id=1236&lvl=3&keep=1&srchmode=1&unlock) can be used. A bacterium belonging to the genus of *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli*(*E. coli*).

The bacterium belonging to the genus *Escherichia* that can be used in the present invention is not particularly limited, however for example, bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on nucleotide sequence analysis of 16S rRNA, etc. (Int. J. Syst. Bacteriol., 43, 162-173 (1993)).

The phrase "bacterium has been modified to attenuate expression of the csrA gene" means that the bacterium has been modified in such a way that the modified bacterium contains a reduced amount of the CsrA protein as compared with an unmodified bacterium, or the modified bacterium is unable to synthesize the CsrA protein. The phrase "bacterium has been modified to attenuate expression of the csrA gene" also means that the target gene is modified in such a way that the modified gene encodes a mutant CsrA protein which has a decreased activity.

The phrases "inactivation of the csrA gene" means that such modified gene encodes a completely non-functional protein. It is also possible that the modified DNA region is unable to naturally express the gene due to the deletion of a part of the gene, the shifting of the reading frame of the gene, the introduction of missense/nonsense mutation(s), or the modification of an adjacent region of the gene, including sequences controlling gene expression, such as promoter, enhancer, attenuator, ribosome-binding site, etc.

The csrA gene encodes a CsrA protein—a carbon storage regulator. The csrA gene of *E. coli* (nucleotides complemented to nucleotides 2816983 to 2817168 in the GenBank accession number NC_000913.2; gi:49175990) is located between the yqaB ORF and the alaS gene on the chromosome of *E. coli* K-12. The nucleotide sequence of the csrA gene and the amino acid sequence of CsrA encoded by the csrA gene are shown in SEQ ID NO:1 and SEQ ID NO:2, respectively.

Since there may be some differences in DNA sequences between the genera or strains of the Enterobacteriaceae family, the csrA gene to be inactivated on the chromosome is not limited to the gene shown in SEQ ID No:1, but may include homologous genes to SEQ ID No:1 encoding a variant protein of the CsrA protein. The phrase "variant protein" as used in the present invention means a protein which has changes in the sequence, whether they are deletions, insertions, additions, or substitutions of amino acids, but still maintains the activity of the product as the CsrA protein. The number of changes in the variant protein depends on the position or the type of amino acid residues in the three dimensional structure of the protein. It may be 1 to 30, preferably 1 to 15, and more preferably 1 to 5 in SEQ ID NO: 2. These changes in the variants can occur in regions of the protein which are not critical for the function of the protein. This is because some amino acids have high homology to one another so the three dimensional structure or activity is not affected by such a change. These changes in the variant protein can occur in regions of the protein which are not critical for the function of the protein. Therefore, the protein variant encoded by the csrA gene may have a homology of not less than 80%, preferably not less than 90%, and most preferably not less than 95%, with respect to the entire amino acid sequence encoded shown in SEQ ID NO. 2, as long as the activity of the CsrA protein prior to inactivation is maintained.

Homology between two amino acid sequences can be determined using the well-known methods, for example, the computer program BLAST 2.0, which calculates three parameters: score, identity and similarity.

Moreover, the csrA gene may be a variant which hybridizes under stringent conditions with the nucleotide sequence shown in SEQ ID NO: 1, or a probe which can be prepared from the nucleotide sequence, provided that it encodes a functional CsrA protein prior to inactivation. "Stringent conditions" include those under which a specific hybrid, for example, a hybrid having homology of not less than 60%, preferably not less than 70%, more preferably not less than 80%, still more preferably not less than 90%, and most preferably not less than 95%, is formed and a non-specific hybrid, for example, a hybrid having homology lower than the above, is not formed. For example, stringent conditions are exemplified by washing one time or more, preferably two or three times at a salt concentration of 1×SSC, 0.1% SDS, preferably 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected depending on the hybridization conditions, and is usually 100 bp to 1 kbp.

Expression of the csrA gene can be attenuated by introducing a mutation into the gene on the chromosome so that intracellular activity of the protein encoded by the gene is decreased as compared with an unmodified strain. Such a mutation on the gene can be replacement of one base or more to cause amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (J. Biol. Chem., 1997, 272 (13): 8611-8617, J. Antimicrobial Chemotherapy, 2000, 46: 793-79). Expression of the csrA gene can also be attenuated by modifying an expression regulating sequence such as the promoter, the Shine-Dalgarno (SD) sequence, etc. (WO95/34672, Biotechnol. Prog. 1999, 15, 58-64).

For example, the following methods may be employed to introduce a mutation by gene recombination. A mutant gene encoding a mutant protein having a decreased activity is prepared, and a bacterium to be modified is transformed with a DNA fragment containing the mutant gene. Then the native gene on the chromosome is replaced with the mutant gene by homologous recombination, and the resulting strain is selected. Such gene replacement using homologous recombination can be conducted by the method employing a linear DNA, which is known as "Red-driven integration" (Proc. Natl. Acad. Sci. USA, 2000, 97 (12): 6640-6645, WO2005/010175), or by the method employing a plasmid containing a temperature-sensitive replication control region (Proc. Natl. Acad. Sci. USA, 2000, 97 (12): 6640-6645, U.S. Pat. Nos. 6,303,383 and 5,616,480). Furthermore, introduction of a site-specific mutation by gene replacement using homologous recombination as set forth above can also be performed by using a plasmid which is unable to replicate in the host.

Expression of the gene can also be attenuated by insertion of a transposon or an IS factor into the coding region of the gene (U.S. Pat. No. 5,175,107), or by conventional methods, such as mutagenesis treatment with UV irradiation or nitrosoguanidine (N-methyl-N'-nitro-N-nitrosoguanidine).

The presence of activity of the CsrA protein can be detected by, for example, complementation of a csrA mutation. A bacterium containing a mutation in the csrA gene will exhibit a much higher level of glycogen accumulation, which can be measured by the method described by, for example, Romeo, T et al (J. Bacteriol., 175(15): 4744-4755 (1993)). Therefore, the reduced or absent activity of the CsrA protein in the bacterium according the present invention can be determined when compared to the parent unmodified bacterium.

The presence or absence of the csrA gene on the chromosome of a bacterium can be detected by well-known methods, including PCR, Southern blotting and the like. In addition, the level of gene expression can be estimated by measuring the amount of mRNA transcribed from the gene using various known methods including Northern blotting, quantitative RT-PCR, and the like. The amount or molecular weight of the protein encoded by the gene can be measured by known methods including SDS-PAGE followed by immunoblotting assay (Western blotting analysis) and the like.

Methods for preparation of plasmid DNA, digestion and ligation of DNA, transformation, selection of an oligonucleotide as a primer and the like may be ordinary methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

L-Amino Acid Producing Bacteria

As a bacterium of the present invention which is modified to attenuate expression of the csrA gene, bacteria which are able to produce a non-aromatic L-amino acid may be used.

The bacterium of the present invention can be obtained by attenuating expression of the csrA gene in a bacterium which inherently has the ability to produce a non-aromatic L-amino acid. Alternatively, the bacterium of present invention can be obtained by imparting the ability to produce a non-aromatic L-amino acid to a bacterium already having attenuated expression of the csrA gene.

L-Threonine-Producing Bacteria

Examples of parent strains for deriving the L-threonine-producing bacteria of the present invention include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Nagatinskaya Street 3-A, 117105 Moscow, Russian Federation) under the accession number RIA 1867. The strain was also deposited in the Russian National Collection of Industrial Microorganisms (VKPM) (Russia, 117545 Moscow 1, Dorozhny proezd. 1) on Apr. 7, 1987 under the accession number B-3996.

*E. coli* VKPM B-5318 (EP 0593792B) may also be used as a parent strain for deriving L-threonine-producing bacteria of the present invention. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

Preferably, the bacterium of the present invention is additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes functions as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feed back inhibition by threonine, as well as, the thrB and thrC genes can be obtained as one operon from well-known plasmid pVIC40 which is present in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17$^{th}$ International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the culture medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains for deriving L-lysine-producing bacteria of the present invention also include strains in which expression of one or more genes encoding an L-lysine biosynthetic enzyme are enhanced. Examples of the enzymes involved in L-lysine biosynthesis include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains may have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria of the present invention also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase, lysine decarboxylase (U.S. Pat. No. 5,827, 698), and the malic enzyme (WO2005/010175).

L-Cysteine-Producing Bacteria

Examples of parent strains for deriving L-cysteine-producing bacteria of the present invention include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (WO0127307A1), and the like.

L-Leucine-Producing Bacteria

Examples of parent strains for deriving L-leucine-producing bacteria of the present invention include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β3-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium of the present invention may be improved by enhancing the expression of one or more genes involved in L-leucine biosynthesis. Examples include genes of the leuABCD operon, which are preferably represented by a mutant leuA gene coding for isopropylmalate synthase not subject to feedback inhibition by L-leucine (U.S. Pat. No. 6,403,342). In addition, the bacterium of the present invention may be improved by enhancing the expression of one or more genes coding for proteins which excrete L-amino acids from the bacterial cell. Examples of such genes include the b2682 and b2683 genes (ygaZH genes) (EP 1239041 A2).

L-Histidine-Producing Bacteria

Examples of parent strains for deriving L-histidine-producing bacteria of the present invention include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains for deriving L-histidine-producing bacteria of the present invention also include strains in which expression of one or more genes encoding an L-histidine biosynthetic enzyme are enhanced. Examples of the L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore an L-histidine-producing ability can also be efficiently enhanced by introducing a mutation conferring resistance to the feedback inhibition into ATP phosphoribosyltransferase (hisG) (Russian Patent Nos. 2003677 and 2119536).

Specific examples of strains having an L-histidine-producing ability include *E. coli* FERM-P 5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria of the present invention include, but are not limited to, strains belonging to the genus *Escherichia*, such as *E. coli* VL334thrC⁺ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC⁺ (VKPM B-8961) was obtained. This strain is able to produce L-glutamic acid.

Examples of parent strains for deriving the L-glutamic acid-producing bacteria of the present invention include, but are not limited to, strains in which expression of one or more genes encoding an L-glutamic acid biosynthetic enzyme are enhanced. Examples of the enzymes involved in L-glutamic acid biosynthesis include glutamate dehydrogenase, glutamine synthetase, glutamate synthetase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, and glucose phosphate isomerase.

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria of the present invention also include strains having decreased or eliminated activity of an enzyme that catalyzes synthesis of a compound other than L-glutamic acid, and branching off from an L-glutamic acid biosynthesis pathway. Examples of such enzymes include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase. Bacteria belonging to the genus *Escherichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is a strain obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria, include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of the Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Proline-Producing Bacteria

Examples of parent strains for deriving L-proline-producing bacteria of the present invention include, but are not limited to, strains belonging to the genus *Escherichia*, such as *E. coli* 702ilvA (VKPM B-8012) which is deficient in the ilvA gene and is able to produce L-proline (EP 1172433). The bacterium of the present invention may be improved by enhancing the expression of one or more genes involved in L-proline biosynthesis. Examples of such genes for L-proline producing bacteria which are preferred include the proB gene coding for glutamate kinase which is desensitized to feedback inhibition by L-proline (DE Patent 3127361). In addition, the bacterium of the present invention may be improved by enhancing the expression of one or more genes coding for proteins excreting L-amino acids from bacterial cells. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains for deriving L-arginine-producing bacteria of the present invention include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthetase is introduced therein (EP1170361A1), and the like.

Examples of parent strains for deriving L-arginine producing bacteria of the present invention also include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase.

L-Valine-Producing Bacteria

Example of parent strains for deriving L-valine-producing bacteria of the present invention include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine-producing bacteria of the present invention include also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd.) on Jun. 24, 1988 under accession number VKPM B-4411.

Furthermore, mutants requiring lipoic acid for growth and/or lacking H$^+$-ATPase can also be used as parent strains (WO96/06926).

L-Isoleucine-Producing Bacteria

Examples of parent strains for deriving L-isoleucine producing bacteria of the present invention include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2 Method of the Present Invention

The method of the present invention is a method for producing an L-amino acid comprising cultivating the bacterium of the present invention in a culture medium to produce and excrete the L-amino acid into the medium, and collecting the L-amino acid from the medium.

In the present invention, the cultivation, collection, and purification of an L-amino acid from the medium and the like may be performed in a manner similar to conventional fermentation methods wherein an amino acid is produced using a bacterium.

A medium used for culture may be either a synthetic or natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the used microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated csrA Gene

1. Deletion of the csrA Gene.

A strain having deletion of the csrA gene was constructed by the method initially developed by Datsenko, K. A. and Wanner, B. L. (Proc. Natl. Acad. Sci. USA, 2000, 97(12), 6640-6645) called "Red-driven integration". According to this procedure, the PCR primers csrAL (SEQ ID NO: 3) and csrAR (SEQ ID NO: 4) which are homologous to both the regions adjacent to the csrA gene and the gene conferring antibiotic resistance, respectively, in the template plasmid, were constructed. The plasmid pACYC184 (NBL Gene Sciences Ltd., UK) (GenBank/EMBL accession number X06403) was used as a template in the PCR reaction. Conditions for PCR were as follows: denaturation step: 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

Figure 1:
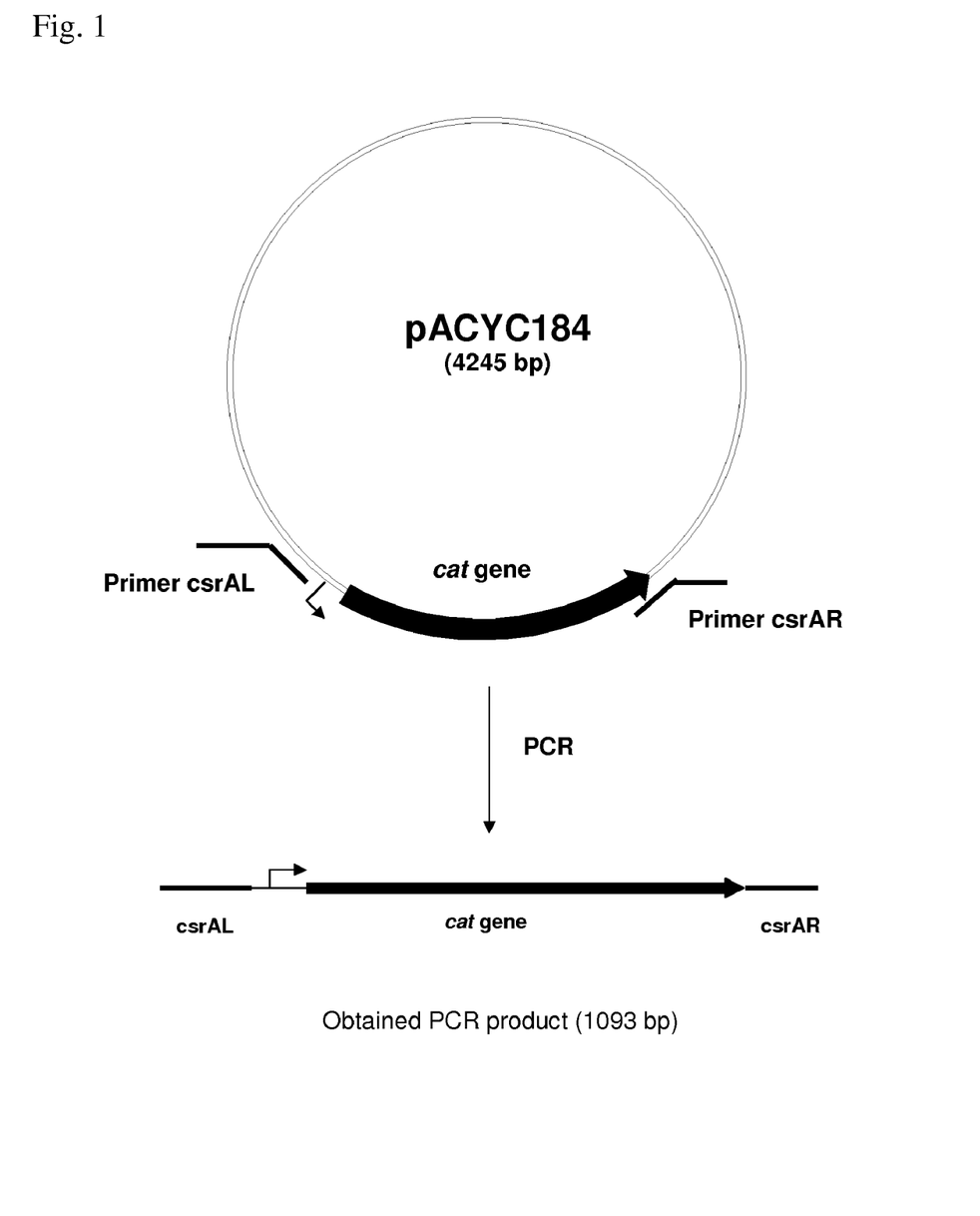
FIG. 1 shows the relative positions of primers csrAL and csrAR on plasmid pACYC184, which is used for amplification of the cat gene.

A 1093 bp PCR product (FIG. 1) was obtained and was purified in agarose gel and was used for electroporation of *E. coli* MG1655 (ATCC 700926), which contains the plasmid pKD46 having a temperature-sensitive replication origin. The plasmid pKD46 (Datsenko, K. A. and Wanner, B. L., Proc. Natl. Acad. Sci. USA, 2000, 97:12:6640-45) includes a 2,154 nucleotide (31088-33241) DNA fragment of phage λ (GenBank accession No. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655.

Electrocompetent cells were prepared as follows: a night culture of *E. coli* MG1655/pKD46 was grown overnight at 30° C. in LB medium containing 100 mg/l of ampicillin, and the culture was diluted 100 times with 5 ml of SOB medium (Sambrook et al, "Molecular Cloning A Laboratory Manual, Second Edition", Cold Spring Harbor Laboratory Press (1989)) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 µl of cells and ≈100 ng of PCR product. Cells after electroporation were incubated with 1 ml of SOC medium (Sambrook et al, "Molecular Cloning A Laboratory Manual, Second Edition", Cold Spring Harbor Laboratory Press (1989)) at 37° C. for 2.5 hours and then were plated onto L-agar containing chloramphenicol (30 µg/ml) and grown at 37° C. to select $Cm^R$ recombinants. Then, to eliminate the pKD46 plasmid, 2 passages on L-agar with Cm at 42° C. were performed and the obtained colonies were tested for sensitivity to ampicillin.

2. Verification of the csrA Gene Deletion by PCR.

Figure 2:
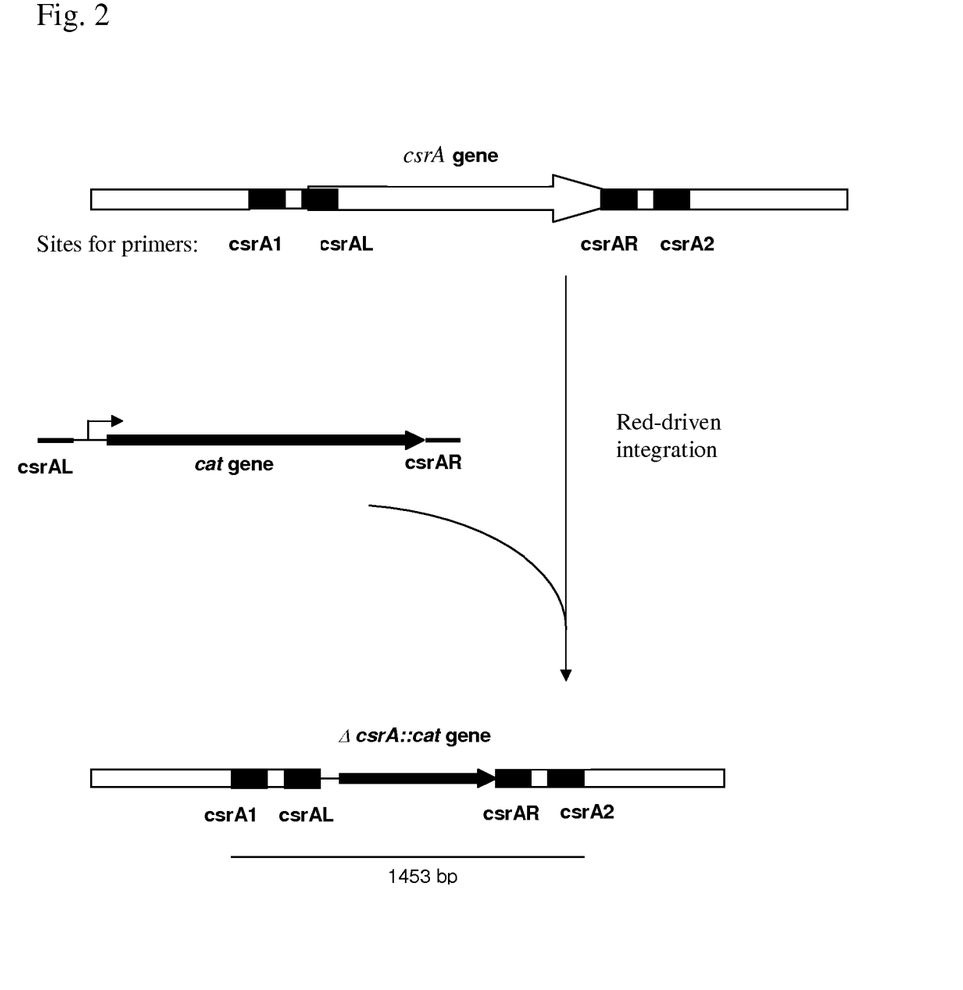
FIG. 2 shows the construction of the chromosomal DNA fragment comprising the inactivated csrA gene.

The mutants, which have the csrA gene deleted, marked with the Cm resistance gene, were verified by PCR. Locus-specific primers csrA1 (SEQ ID NO: 5) and csrA2 (SEQ ID NO: 6) were used in PCR for verification. Conditions for PCR verification were as follows: denaturation step: 3 min at 94° C.; profile for the 30 cycles: 30 sec at 94° C., 30 sec at 54° C., 1 min at 72° C.; final step: 7 min at 72° C. The PCR product obtained in the reaction with the cells of the parental $csrA^+$ strain MG1655 as the template was 547 bp in length. The PCR product obtained in the reaction with the cells of the mutant strain as the template was 1453 bp in length (FIG. 2). The mutant strain was named MG1655 ΔcsrA::cat.

Example 2

Production of L-Threonine by *E. coli* B-3996-ΔcsrA

To test the effect of inactivation of the csrA gene on threonine production, DNA fragments from the chromosome of the above-described *E. coli* MG1655 ΔcsrA::cat were transferred to the threonine-producing *E. coli* strain VKPM B-3996 by P1 transduction (Miller, J. H. (1972) Experiments in Molecular Genetics, Cold Spring Harbor Lab. Press, Plainview, N.Y.) to obtain the strain B-3996-ΔcsrA.

Both *E. coli* B-3996 and B-3996-ΔcsrA were grown for 18-24 hours at 37° C. on L-agar plates. To obtain a seed culture, the strains were grown on a rotary shaker (250 rpm) at 32° C. for 18 hours in 20×200 mm test tubes containing 2 ml of L-broth with 4% sucrose. Then, the fermentation medium was inoculated with 0.21 ml (10%) seed material. The fermentation was performed in 2 ml of minimal medium for fermentation in 20×200 mm test tubes. Cells were grown for 65 hours at 32° C. with shaking at 250 rpm.

After cultivation, the amount of L-threonine which had accumulated in the medium was determined by paper chromatography using the following mobile phase: butanol:acetic acid:water=4:1:1 (v/v). A solution (2%) of ninhydrin in acetone was used as a visualizing reagent. A spot containing L-threonine was cut out, L-threonine was eluted in 0.5% water solution of $CdCl_2$, and the amount of L-threonine was estimated spectrophotometrically at 540 nm. The results of 10 independent test tube fermentations are shown in Table 1.

The composition of the fermentation medium (g/l) was as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4\,7H_2O$ | 0.8 |
| $FeSO_4\,7H_2O$ | 0.02 |
| $MnSO_4\,5H_2O$ | 0.02 |
| Thiamine HCl | 0.0002 |
| Yeast extract | 1.0 |
| $CaCO_3$ | 30.0 |

Glucose and magnesium sulfate were sterilized separately. $CaCO_3$ was sterilized by dry-heat at 180° C. for 2 hours. The pH was adjusted to 7.0. Antibiotic was introduced into the medium after sterilization.

TABLE 1

| Strain | $OD_{540}$ | Amount of L-threonine, g/l |
|---|---|---|
| B-3996 | 26.1 ± 0.5 | 23.4 ± 0.4 |
| B-3996-ΔcsrA | 27.2 ± 1.8 | 24.8 ± 0.9 |

It can be seen from Table 1 that B-3996-ΔcsrA caused accumulation of a higher amount of L-threonine as compared with B-3996.

Example 3

Production of L-Lysine by *E. coli* WC196 (pCABD2)-ΔcsrA

To test the effect of inactivation of the csrA gene on lysine production, DNA fragments from the chromosome of the above-described *E. coli* MG1655 ΔcsrA::cat can be transferred to the lysine-producing *E. coli* strain WC196 (pCABD2) by P1 transduction (Miller, J. H. (1972) Experiments in Molecular Genetics, Cold Spring Harbor Lab. Press, Plainview, N.Y.) to obtain the strain WC196(pCABD2)-ΔcsrA::cat. pCABD2 is a plasmid which includes a dapA gene coding for a dihydrodipicolinate synthase having a mutation which desensitizes feedback inhibition by L-lysine, a lysC gene coding for aspartokinase III having a mutation which desensitizes feedback inhibition by L-lysine, a dapB gene coding for a dihydrodipicolinate reductase gene, a ddh gene coding for diaminopimelate dehydrogenase, and a streptomycin resistance gene (U.S. Pat. No. 6,040,160).

Both *E. coli* WC196(pCABD2) and WC196(pCABD2) ΔcsrA::cat can be cultured in the L-medium containing 20 mg/l of streptomycin at 37° C. 0.3 ml of the obtained cultures can each be inoculated into 20 ml of the fermentation medium containing the required drugs in a 500 ml-flask. The cultivation can be carried out at 37° C. for 16 hours by using a reciprocal shaker at the agitation speed of 115 rpm. After the cultivation, the amounts of L-lysine and residual glucose in the medium can be measured by a known method (Biotech-analyzer AS210, manufactured by Sakura Seiki Co.). Then, the yield of L-lysine relative to consumed glucose can be calculated for each of the strains.

The composition of the fermentation medium (g/l) is as follows:

| | |
|---|---|
| Glucose | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 | pH is adjusted to 7.0 by KOH and the medium is autoclaved at 115° C. for 10 min. Glucose and $MgSO_4.7H_2O$ are sterilized separately. 30 µl of $CaCO_3$, which has been dry-heat sterilized at 180° C. for 2 hours, is added.

Example 4

Production of L-Cysteine by *E. coli* JM15(ydeD)-ΔcsrA

To test the effect of inactivation of the csrA gene on L-cysteine production, DNA fragments from the chromosome of the above-described *E. coli* MG1655 ΔcsrA::cat can be transferred to the *E. coli* L-cysteine producing strain JM15(ydeD) by P1 transduction (Miller, J. H. (1972) Experiments in Molecular Genetics, Cold Spring Harbor Lab. Press, Plainview, N.Y.) to obtain the strain JM15(ydeD)-ΔcsrA. The strain JM15 (CGSC# 5042) can be obtained from The Coli Genetic Stock Collection at the *E. coli* Genetic Resource Center, MCD Biology Department, Yale University (http://cgsc.biology.yale.edu/).

*E. coli* JM15(ydeD) is a derivative of *E. coli* JM15 (U.S. Pat. No. 6,218,168) which can be transformed with DNA having the ydeD gene, which codes for a membrane protein, and is not involved in a biosynthetic pathway of any L-amino acid (U.S. Pat. No. 5,972,663).

Fermentation conditions for evaluation of L-cysteine production are described in detail in Example 6 of U.S. Pat. No. 6,218,168.

Example 5

Production of L-Leucine by *E. coli* 57-ΔcsrA

To test the effect of inactivation of the csrA gene on L-leucine production, DNA fragments from the chromosome of the above-described *E. coli* MG1655 ΔcsrA::cat can be transferred to the *E. coli* L-leucine producing strain 57 (VKPM B-7386, U.S. Pat. No. 6,124,121) can be performed by P1 transduction (Miller, J. H. (1972) Experiments in Molecular Genetics, Cold Spring Harbor Lab. Press, Plainview, N.Y.) to obtain the strain 57-pMW-ΔcsrA. The strain 57 has been deposited in the Russian National Collection of Industrial Microorganisms (VKPM) (Russia, 117545 Moscow, 1 Dorozhny proezd, 1) on May 19, 1997 under accession number VKPM B-7386.

Both *E. coli* 57 and 57-ΔcsrA can be cultured for 18-24 hours at 37° C. on L-agar plates. To obtain a seed culture, the strains can be grown on a rotary shaker (250 rpm) at 32° C. for 18 hours in 20×200 mm test tubes containing 2 ml of L-broth with 4% sucrose. Then, the fermentation medium can be inoculated with 0.21 ml (10%) seed material. The fermentation can be performed in 2 ml of minimal medium for fermentation in 20×200 mm test tubes. Cells can be grown for 48-72 hours at 32° C. with shaking at 250 rpm. The amount of L-leucine can be measured by paper chromatography (liquid phase composition: butanol-acetic acid-water=4:1:1)

The composition of the fermentation medium (g/l) is as follows (pH 7.2):

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine | 0.01 |
| $CaCO_3$ | 25.0 |

Glucose and $CaCO_3$ are be sterilized separately.

Example 6

Production of L-Histidine by *E. coli* 80-ΔcsrA

To test the effect of inactivation of the csrA gene on L-histidine production, DNA fragments from the chromosome of the above-described *E. coli* MG1655 ΔcsrA::cat were transferred to the histidine-producing *E. coli* strain 80 by P1 transduction (Miller, J. H. (1972) Experiments in Molecular Genetics, Cold Spring Harbor Lab. Press, Plainview, N.Y.) to obtain the strain 80-ΔcsrA. The strain 80 has been described in Russian patent 2119536 and deposited in the Russian National Collection of Industrial Microorganisms (Russia, 117545 Moscow, 1 Dorozhny proezd, 1) on Oct. 15, 1999 under accession number VRPM B-7270 and then converted to a deposit under the Budapest Treaty on Jul. 12, 2004.

For mini-jar batch-fermentation one loop of each strain, 80 and 80-ΔcsrA, grown on L-agar was transferred to L-broth and cultivated at 30° C. with rotation (140 rpm) to reach optical density of culture $OD_{540} \approx 2.0$. Then 25 ml of seed culture was added to 250 ml of medium for fermentation and cultivated at 29° C. with rotation (1500 rpm). The duration of the batch-fermentation was approximately 35-40 hours. After the cultivation, the amount of histidine which had accumulated in the medium was determined by paper chromatography. The paper was developed with a mobile phase: n-butanol:acetic acid:water=4:1:1 (v/v). A solution of ninhydrin (0.5%) in acetone was used as a visualizing reagent. Obtained data are presented in the Table 2.

The composition of the fermentation medium (g/l) is as follows (pH 6.0):

| | |
|---|---|
| Glucose | 100.0 |
| Mameno (soybean hydrolysate) | 0.2 as total nitrogen |

-continued

| | |
|---|---|
| (NH$_4$)$_2$SO$_4$ | 8.0 |
| KH$_2$PO$_4$ | 1.0 |
| MgSO$_4$•7H$_2$0 | 0.4 |
| FeSO$_4$•7H$_2$0 | 0.02 |
| MnSO$_4$ | 0.02 |
| Thiamine | 0.001 |
| Betaine | 2.0 |
| L-proline | 0.8 |
| L-glutamate | 3.0 |
| L-aspartate | 1.0 |
| Adenosine | 0.1 |

TABLE 2

| Strain | Amount of L-histidine, g/l | Average yield from glucose, % |
|---|---|---|
| 80 | 16.8 ± 0.5 | 20.3 |
| 80-ΔcsrA | 18.0 ± 0.6 | 22.3 |

It can be seen from Table 2 that strain 80-ΔcsrA caused accumulation of a higher amount of L-histidine as compared with strain 80.

Example 7

Production of L-Glutamate by E. coli VL334thrC$^+$-ΔcsrA

To test the effect of inactivation of the csrA gene on L-glutamate production, DNA fragments from the chromosome of the above-described E. coli MG1655 ΔcsrA::cat can be transferred to the E. coli L-glutamate producing strain VL334thrC$^+$ (EP 1172433) by P1 transduction (Miller, J. H. (1972) Experiments in Molecular Genetics, Cold Spring Harbor Lab. Press, Plainview, N.Y.) to obtain the strain VL334thrC$^+$-ΔcsrA. The strain L334thrC$^+$ has been deposited in the Russian National Collection of Industrial Microorganisms (VKPM) (Russia, 117545 Moscow, 1 Dorozhny proezd, 1) on Dec. 6, 2004 under the accession number VKPM B-8961 and then converted to a deposit under the Budapest Treaty on Dec. 8, 2004.

Both strains, VL334thrC$^+$ and VL334thrC$^+$-ΔcsrA, can be grown for 18-24 hours at 37° C. on L-agar plates. Then, one loop of the cells can be transferred into test tubes containing 2 ml of fermentation medium. The fermentation medium contains 60 g/l glucose, 25 g/l ammonium sulfate, 2 g/l KH$_2$PO$_4$, 1 g/l MgSO$_4$, 0.1 mg/ml thiamine, 70 μg/ml L-isoleucine and 25 μl CaCO$_3$ (pH 7.2). Glucose and CaCO$_3$ should be sterilized separately. Cultivation can be carried out at 30° C. for 3 days with shaking. After the cultivation, the amount of L-glutamic acid produced can be determined by paper chromatography (liquid phase composition: butanol-acetic acid-water=4:1:1) with subsequent staining by ninhydrin (1% solution in acetone) and further elution of the compounds in 50% ethanol with 0.5% CdCl$_2$.

Example 8

Production of L-Proline by E. coli 702ilvA-ΔcsrA

To test the effect of inactivation of the csrA gene on L-proline production, DNA fragments from the chromosome of the above-described E. coli MG1655 ΔcsrA::cat can be transferred to the proline-producing E. coli strain 702ilvA by P1 transduction (Miller, J. H. (1972) Experiments in Molecular Genetics, Cold Spring Harbor Lab. Press, Plainview, N.Y.) to obtain the strain 702ilvA-ΔcsrA. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

Both E. coli 702ilvA and 702ilvA-ΔcsrA can be grown for 18-24 hours at 37° C. on L-agar plates. Then, these strains can be cultivated under the same conditions as in Example 7.

Example 9

Production of L-Arginine by E. coli 382-ΔcsrA

To test the effect of inactivation of the csrA gene on L-arginine production, DNA fragments from the chromosome of the above-described E. coli MG1655 ΔcsrA::cat can be transferred to the arginine-producing E. coli strain 382 by P1 transduction (Miller, J. H. (1972) Experiments in Molecular Genetics, Cold Spring Harbor Lab. Press, Plainview, N.Y.) to obtain the strain 382-ΔcsrA. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

Both strains, 382-ΔcsrA and 382, can be each cultivated at 32° C. for 18 hours in 2 ml of LB nutrient broth, and 0.3 ml of the obtained culture can be inoculated into 2 ml of fermentation medium in a 20×200 mm test tube, and cultivated at 32° C. for 48 hours on a rotary shaker.

After the cultivation, the amount of L-arginine which accumulates in the medium can be determined by paper chromatography using the following mobile phase: butanol:acetic acid:water ratio—4:1:1 (v/v). A solution (2%) of ninhydrin in acetone can be used as a visualizing reagent. A spot containing L-arginine can be cut out, L-arginine can be eluted in 0.5% water solution of CdCl$_2$, and the amount of L-arginine can be determined spectrophotometrically at 540 nm.

The composition of the fermentation medium (g/l) is as follows:

| | |
|---|---|
| Glucose | 48.0 |
| (NH4)$_2$SO$_4$ | 35.0 |
| KH$_2$PO$_4$ | 2.0 |
| MgSO$_4$•7H$_2$O | 1.0 |
| Thiamine HCl | 0.0002 |
| Yeast extract | 1.0 |
| L-isoleucine | 0.1 |
| CaCO3 | 5.0 |

Glucose and magnesium sulfate are sterilized separately. CaCO$_3$ is sterilized by dry-heat at 180° C. for 2 hours. pH is adjusted to 7.0.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of a non-aromatic L-amino acid of a bacterium of the Enterobacteriaceae family can be enhanced.

The invention claimed is:

1. A method for producing a non-aromatic L-amino acid selected from the group consisting of L-threonine, L-histidine and combinations thereof, comprising:
cultivating a non-aromatic L-amino acid producing *Escherichia coli* bacterium in a medium to produce and excrete said non-aromatic L-amino acid into the medium, and
collecting said non-aromatic L-amino acid from the medium,
wherein the bacterium has been modified to attenuate expression of the csrA gene by a method selected from the group consisting of:
A) deleting the csrA gene,
B) introducing one or more mutations into the csrA gene,
C) modifying an expression regulating sequence of the csrA gene, and
D) combinations thereof; and
wherein the csrA gene is the *Escherichia coli* csrA gene.

2. The method according to claim 1, wherein the csrA gene encodes a protein selected from the group consisting of:
(A) a protein comprising the amino acid sequence of SEQ ID NO: 2,
(B) a protein with homology of not less than 95% to the amino acid sequence of SEQ ID NO: 2, and wherein said protein has CsrA protein activity.

3. The method according to claim 2, wherein the csrA gene encodes a protein comprising the amino acid sequence of SEQ ID NO: 2.

4. The method according to claim 2, wherein the non-aromatic L-amino acid is L-threonine,
and wherein the bacterium has been further modified to enhance expression of a gene selected from the group consisting of:
A) a mutant thrA gene encoding for aspartokinase homoserine dehydrogenase I resistant to feedback inhibition by threonine,
B) the thrB gene encoding homoserine kinase,
C) the thrC gene encoding threonine synthase,
D) the rhtA gene encoding a putative transmembrane protein, and
E) combinations thereof.

5. The method according to claim 2, wherein the non-aromatic L-amino acid is L-histidine,
and wherein the bacterium has been further modified to enhance expression of a gene selected from the group consisting of:
A) the hisG gene encoding ATP phosphoribosyltransferase,
B) the hisI gene encoding phosphoribosyl AMP cyclohydrolase,
C) the hisIE gene encoding forphosphoribosyl-ATP pyrophosphohydrolase,
D) the hisA gene encoding phosphoribosylformimino-5-aminoimidazole carboxamide ribotide isomerase,
E) the hisH gene encoding amidotransferase,
F) the hisC gene encoding histidinol phosphate aminotransferase,
G) the hisB gene encoding histidinol phosphatase,
H) the hisD gene encoding histidinol dehydrogenase, and
I) combinations thereof.

* * * * *

SEQUENCE LISTING

<160> NUMBER OF SEQ ID NOS: 6

<210> SEQ ID NO 1
<211> LENGTH: 186
<212> TYPE: DNA
<213> ORGANISM: Escherichia coli
<220> FEATURE:
<221> NAME/KEY: CDS
<222> LOCATION: (1)..(186)

<400> SEQUENCE: 1

```
atg ctg att ctg act cgt cga gtt ggt gag acc ctc atg att ggg gat        48
Met Leu Ile Leu Thr Arg Arg Val Gly Glu Thr Leu Met Ile Gly Asp
1               5                   10                  15 gag gtc acc gtg aca gtt tta ggg gta aag ggc aac cag gta cgt att        96
Glu Val Thr Val Thr Val Leu Gly Val Lys Gly Asn Gln Val Arg Ile
            20                  25                  30 ggc gta aat gcc ccg aag gaa gtt tct gtt cac cgt gaa gag atc tac       144
Gly Val Asn Ala Pro Lys Glu Val Ser Val His Arg Glu Glu Ile Tyr
        35                  40                  45 cag cgt atc cag gct gaa aaa tcc cag cag tcc agt tac taa               186
Gln Arg Ile Gln Ala Glu Lys Ser Gln Gln Ser Ser Tyr
    50                  55                  60
```

<210> SEQ ID NO 2
<211> LENGTH: 61
<212> TYPE: PRT
<213> ORGANISM: Escherichia coli

<400> SEQUENCE: 2

```
Met Leu Ile Leu Thr Arg Arg Val Gly Glu Thr Leu Met Ile Gly Asp
1               5                   10                  15

Glu Val Thr Val Thr Val Leu Gly Val Lys Gly Asn Gln Val Arg Ile
            20                  25                  30

Gly Val Asn Ala Pro Lys Glu Val Ser Val His Arg Glu Glu Ile Tyr
        35                  40                  45

Gln Arg Ile Gln Ala Glu Lys Ser Gln Gln Ser Ser Tyr
    50                  55                  60
```

<210> SEQ ID NO 3
<211> LENGTH: 59
<212> TYPE: DNA
<213> ORGANISM: Artificial
<220> FEATURE:
<223> OTHER INFORMATION: primer

<400> SEQUENCE: 3
ttagtaactg gactgctggg atttttcagc ctggattgat gtccggcggt gcttttgcc        59

<210> SEQ ID NO 4
<211> LENGTH: 57
<212> TYPE: DNA
<213> ORGANISM: Artificial
<220> FEATURE:
<223> OTHER INFORMATION: primer

<400> SEQUENCE: 4
aatgctgatt ctgactcgtc gagttggtga gacccttac gccccgccct gccactc           57

<210> SEQ ID NO 5
<211> LENGTH: 23
<212> TYPE: DNA

```
<213> ORGANISM: Artificial
<220> FEATURE:
<223> OTHER INFORMATION: primer

<400> SEQUENCE: 5
caacagaaga atggaggtct gac                                         23

<210> SEQ ID NO 6
<211> LENGTH: 19
<212> TYPE: DNA
<213> ORGANISM: Artificial
<220> FEATURE:
<223> OTHER INFORMATION: primer

<400> SEQUENCE: 6
gtggactcgc ttcacggca                                              19
```